United States Patent
Sinofsky (10) Patent No.: US 6,676,656 B2
(45) Date of Patent: *Jan. 13, 2004

(54) SURGICAL ABLATION WITH RADIANT ENERGY

(75) Inventor: Edward L. Sinofsky, Dennis, MA (US)

(73) Assignee: CardioFocus, Inc., Norton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/924,393

(22) Filed: Aug. 7, 2001

(65) Prior Publication Data

US 2002/0077623 A1 Jun. 20, 2002

Related U.S. Application Data

(63) Continuation-in-part of application No. PCT/US01/22299, filed on Jul. 16, 2001, and a continuation-in-part of application No. 09/616,777, filed on Jul. 14, 2000, and a continuation-in-part of application No. 09/390,964, filed on Sep. 7, 1999, now Pat. No. 6,270,492, which is a continuation-in-part of application No. 08/991,130, filed on Dec. 16, 1997, now Pat. No. 5,947,959, which is a continuation-in-part of application No. 08/827,631, filed on Apr. 10, 1997, now Pat. No. 5,908,415, which is a continuation-in-part of application No. 08/303,605, filed on Sep. 9, 1994, now abandoned.

(51) Int. Cl.$^7$ ............................................... A61B 18/18
(52) U.S. Cl. ........................................ 606/16; 128/898
(58) Field of Search ................... 606/1, 2, 3, 7, 606/8, 10, 13–17, 27; 128/898; 607/88–89, 90

(56) References Cited

U.S. PATENT DOCUMENTS

| 4,699,147 A | | 10/1987 | Chilson et al. ............. 128/642 |
| 4,860,743 A | * | 8/1989 | Abela ........................... 606/7 |
| 4,862,886 A | * | 9/1989 | Clarke et al. ................. 606/7 |
| 4,913,142 A | * | 4/1990 | Kittrell et al. ............... 606/15 |
| 5,071,417 A | | 12/1991 | Sinofsky ........................ 606/8 |
| 5,151,096 A | | 9/1992 | Khoury ......................... 606/15 |
| 5,151,097 A | * | 9/1992 | Daikuzono .................... 606/15 |
| 5,163,935 A | | 11/1992 | Black et al. .................. 606/17 |
| 5,219,346 A | | 6/1993 | Wagnieres et al. ............ 606/16 |
| 5,368,564 A | | 11/1994 | Savage ......................... 604/95 |
| 5,380,316 A | * | 1/1995 | Aita et al. ...................... 606/7 |
| 5,411,025 A | | 5/1995 | Webster, Jr. ................. 128/642 |
| 5,431,168 A | | 7/1995 | Webster, Jr. ................. 128/658 |
| 5,431,647 A | | 7/1995 | Purcell, Jr. et al. .......... 606/16 |
| 5,441,497 A | | 8/1995 | Narciso, Jr. .................. 606/15 |
| 5,464,404 A | * | 11/1995 | Abela et al. .................. 606/15 |
| 5,471,982 A | | 12/1995 | Edwards et al. ............. 128/642 |
| 5,482,037 A | * | 1/1996 | Borghi ......................... 600/381 |
| 5,500,012 A | | 3/1996 | Brucker et al. .............. 607/122 |

(List continued on next page.)

FOREIGN PATENT DOCUMENTS

| DE | 9411754.3 | 11/1994 |
| EP | 0792664 | 9/1997 |
| EP | 1072231 | 1/2001 |
| WO | WO 9426184 | 11/1994 |
| WO | 9607451 | 3/1996 |
| WO | WO 0113812 | 3/2001 |

*Primary Examiner*—Linda C. M. Dvorak
*Assistant Examiner*—Peter J Vrettakos
(74) *Attorney, Agent, or Firm*—Thomas J. Engellenner; Lisa J. Michaud; Nutter & McClennen & Fish LLP (57) ABSTRACT

Surgical ablation instruments are disclosed for creating lesions in tissue, including cardiac tissue for treatment of arrhythmias and other diseases. The hand held instruments are especially useful in open chest or port access cardiac surgery for rapid and efficient creation of curvilinear lesions to serve as conduction blocks. Photoablative instruments are disclosed that can achieve rapid and effective photoablation through the use of distributed (e.g., diffuse or defocused) radiant energy.

20 Claims, 10 Drawing Sheets

U.S. PATENT DOCUMENTS

| | | | |
|---|---|---|---|
| 5,507,725 A | 4/1996 | Savage et al. ................. 604/95 |
| 5,536,265 A | 7/1996 | van den Bergh et al. ........ 606/2 |
| 5,542,928 A | 8/1996 | Evans et al. ................. 604/113 |
| 5,575,766 A * | 11/1996 | Swartz et al. ................. 600/16 |
| 5,628,313 A | 5/1997 | Webster, Jr. ................. 128/642 |
| 5,643,253 A | 7/1997 | Baxter et al. ................. 606/17 |
| 5,649,923 A | 7/1997 | Gregory et al. |
| 5,681,280 A | 10/1997 | Rusk et al. ................... 604/95 |
| 5,722,401 A | 3/1998 | Pietroski et al. ............ 128/642 |
| 5,772,590 A | 6/1998 | Webster, Jr. ................. 600/374 |
| 5,779,646 A | 7/1998 | Koblish et al. ............. 600/567 |
| 5,782,239 A | 7/1998 | Webster, Jr. ................. 128/642 |
| 5,782,899 A | 7/1998 | Imran ........................ 607/122 |
| 5,800,482 A | 9/1998 | Pomeranz et al. ........... 607/101 |
| 5,807,395 A | 9/1998 | Mulier et al. ................. 606/41 |
| 5,823,955 A | 10/1998 | Kuck et al. ................. 600/374 |
| 5,824,005 A * | 10/1998 | Motamedi et al. ............ 606/15 |
| 5,830,209 A | 11/1998 | Savage et al. ................. 606/15 |
| 5,833,682 A | 11/1998 | Amplatz et al. .............. 606/15 |
| 5,860,974 A | 1/1999 | Abele .......................... 606/41 |
| 5,931,834 A * | 8/1999 | Murphy-Chutorian et al. ............................ 606/11 |
| 5,938,660 A * | 8/1999 | Swartz et al. ................. 606/45 |
| 6,161,543 A * | 12/2000 | Cox et al. ................... 128/898 |
| 6,237,605 B1 * | 5/2001 | Vaska et al. ................. 128/898 |
| 6,314,962 B1 * | 11/2001 | Vaska et al. ................. 128/898 |
| 6,325,797 B1 * | 12/2001 | Stewart et al. ................ 606/41 |

\* cited by examiner

SURGICAL ABLATION WITH RADIANT ENERGY

CROSS-REFERENCE TO RELATED APPLICATIONS

This application is a continuation-in-part of U.S. patent application Ser. No. 09/616,777, filed on Jul. 14, 2000 and a continuation-in-part of U.S. patent application Ser. No. 09/390,964, filed Sep. 7, 1999 now U.S. Pat No. 6,270,492, which is a continuation-in-part of U.S. patent application Ser. No. 08/991,130, filed Dec. 16, 1997, now U.S. Pat. No. 5,947,595 issued Sep. 7, 1999, which is a continuation-in-part of U.S. patent application Ser. No. 08/827,631, filed Apr. 10, 1997, now U.S. Pat. No. 5,908,415 issued Jun. 1, 1999, which is a continuation-in-part of U.S. patent application Ser. No. 08/303,605, filed Sep. 9, 1994 now abandoned. This application is also a continuation-in-part of International Patent Application No. PCT/US01/22299 filed Jul. 16, 2001.

BACKGROUND OF THE INVENTION

The present invention relates to surgical ablation instruments for ablation of tissue for the treatment of diseases, and, in particular, to surgical instruments employing radiant energy. Methods of ablating tissue using radiant energy are also disclosed. The instruments can be used, for example, in the treatment of cardiac conditions such as cardiac arrhythmias.

Cardiac arrhythmias, e.g., fibrillation, are irregularities in the normal beating pattern of the heart and can originate in either the atria or the ventricles. For example, atrial fibrillation is a form of arrhythmia characterized by rapid randomized contractions of the atrial myocardium, causing an irregular, often rapid ventricular rate. The regular pumping function of the atria is replaced by a disorganized, ineffective quivering as a result of chaotic conduction of electrical signals through the upper chambers of the heart. Atrial fibrillation is often associated with other forms of cardiovascular disease, including congestive heart failure, rheumatic heart disease, coronary artery disease, left ventricular hypertrophy, cardiomyopathy or hypertension.

Various surgical techniques have been proposed for the treatment of arrhythmia. Although these procedures were originally performed with a scalpel, these techniques may also use ablation (also referred to as coagulation) wherein the tissue is treated, generally with heat or cold, to cause tissue necrosis (i.e., cell destruction). The destroyed muscle cells are replaced with scar tissue which cannot conduct normal electrical activity within the heart.

For example, the pulmonary vein has been identified as one of the origins of errant electrical signals responsible for triggering atrial fibrillation. In one known approach, circumferential ablation of tissue within the pulmonary veins or at the ostia of such veins has been practiced to treat atrial fibrillation. Similarly, ablation of the region surrounding the pulmonary veins as a group has also been proposed. By ablating the heart tissue (typically in the form linear or curved lesions) at selected locations, electrical conductivity from one segment to another can be blocked and the resulting segments become too small to sustain the fibrillatory process on their own. Ablation procedures are often performed during coronary artery bypass and mitral valve replacement operations because of a heightened risk of arrhythmias in such patients and the opportunity that such surgery presents for direct access to the heart.

Several types of ablation devices have recently been proposed for creating lesions to treat cardiac arrhythmias, including devices which employ electrical current (e.g., radio-frequency "RF") heating or cryogenic cooling. Such ablation devices have been proposed to create elongated lesions that extend through a sufficient thickness of the myocardium to block electrical conduction.

These devices, however, are not without their drawbacks. When cardiac surgery is performed "on pump," the amount of time necessary to form a lesion becomes a critical factor. Because these devices rely upon resistive and conductive heating (or cooling), they must be placed in direct contact with the heart and such contact must be maintained for a considerable period of time to form a lesion that extends through the entire thickness of the heart muscle. The total length of time to form the necessary lesions can be excessive. This is particularly problematic for procedures that are performed upon a "beating heart" patient. In such cases the heart, itself, continues to beat and, hence, is filled with blood, thus providing a heat sink (or reservoir) that works against conductive and/or resistive ablation devices. As "beating heart" procedures become more commonplace (in order to avoid the problems associated with arresting a patient's heart and placing the patient on a pump), the need for better ablation devices will continue to grow.

Moreover, devices that rely upon resistive or conductive heat transfer can be prone to serious post-operative complications. In order to quickly perform an ablation with such "contact" devices, a significant amount of energy must be applied directly to the target tissue site. In order to achieve transmural penetration, the surface that is contacted will experience a greater degree of heating (or freezing). For example, in RF heating of the heart wall, a transmural lesion requires that the tissue temperature be raised to about 50° C. throughout the thickness of the wall. To achieve this, the contact surface will typically be raised to at least 80° C. Charring of the surface of the heart tissue can lead to the creation of blood clots on the surface which can lead to post-operative complications, including stroke. Even if structural damage is avoided, the extent of the lesion (i.e., the width of the ablated zone) on the surface that has been contacted will typically be greater than necessary.

Ablation devices that do not require direct contact have also been proposed, including acoustic and radiant energy. Acoustic energy (e.g., ultrasound) is poorly transmitted into tissue (unless a coupling fluid is interposed). Laser energy has also been proposed but only in the context of devices that focus light into spots or other patterns. When the light energy is delivered in the form of a focused spot, the process is inherently time consuming because of the need to expose numerous spots to form a continuous linear or curved lesion.

In addition, existing instruments for cardiac ablation also suffer from a variety of design limitations. The shape of the heart muscle adds to the difficulty in accessing cardiac structures, such as the pulmonary veins on the anterior surface of the heart.

Accordingly, there exists a need for better surgical ablation instruments that can form lesions with minimal overheating and/or damage to collateral tissue. Moreover, instruments that are capable of creating lesions uniformly, rapidly and efficiently would satisfy a significant need in the art.

SUMMARY OF THE INVENTION

Surgical ablation instruments are disclosed for creating lesions in tissue, especially cardiac tissue for treatment of arrhythmias and the like. The hand held instruments are especially useful in open chest or port access cardiac surgery for rapid and efficient creation of curvilinear lesions to serve as conduction blocks. The instruments can be applied to form either endocardial or epicardial ablations, and are designed to create lesions in the atrial tissue in order to electrically decouple tissue segments on opposite sides of the lesion.

In one aspect of the invention, hand-held and percutaneous instruments are disclosed that can achieve rapid and effective photoablation through the use of penetrating radiation, especially distributed radiant energy. It has been discovered that radiant energy, e.g., diffuse infrared radiation, can create lesions in less time and with less risk of the adverse types of tissue destruction commonly associated with prior art approaches. Unlike instruments that rely on thermal conduction or resistive heating, controlled penetrating radiant energy can be used to simultaneously deposit energy throughout the full thickness of a target tissue, such as a heart wall, even when the heart is filled with blood. Distributed radiant energy can also produce better defined and more uniform lesions.

It has also been discovered that infrared radiation is particularly useful in forming photoablative lesions. In one preferred embodiment the instruments emit radiation at a wavelength in a range from about 800 nm to about 1000 nm, and preferably emit at a wavelength in a range of about 915 nm to about 980 nm. Radiation at a wavelength of 915 nm or 980 nm is commonly preferred, in some applications, because of the optimal absorption of infrared radiation by cardiac tissue at these wavelengths. In the case of ablative radiation that is directed towards the epicardial surface, light at a wavelength about 915 nm can be particularly preferably.

In another aspect of the invention, surgical ablation instruments are disclosed that are well adapted for use in or around the intricate structures of the heart. In one embodiment, the distal end of the instrument can have a malleable shape so as to conform to the surgical space in which the instrument is used. Optional the distal end of the instrument can be shaped into a curve having a radius between about 5 millimeters and about 25 millimeters. The instruments can include at least one malleable strip element disposed within the distal end of the instrument body or housing so that the distal end can be conformed into a desired shape. In addition, the instruments can also include a clasp to form a closed loop after encircling a target site, such as the pulmonary veins.

In yet another aspect of the invention, surgical ablation instruments are disclosed having a housing with at least one lumen therein and having a distal portion that is at least partially transmissive to photoablative radiation. The instruments further include a light delivery element within the lumen of the housing that is adapted to receive radiation from a source and deliver radiant energy through a transmissive region of the housing to a target tissue site. The radiant energy is delivered without the need for contact between the light emitting element and the target tissue because the instruments of the present invention do not rely upon conductive or resistive heating.

The light delivering element can be a light transmitting optical fiber adapted to receive ablative radiation from a radiation source and a light emitting tip at a distal end of the fiber for emitting diffuse or defocused radiation. The light delivering element can be slidably disposed within the inner lumen of the housing and the instrument can further include a translatory mechanism for disposing the tip of the light delivering element at one or more of a plurality of locations with the housing. Optionally, a lubricating fluid can be disposable between the light delivery element and the housing. This fluid can be a physiologically compatible fluid, such as saline, and the fluid can also be used for cooling the light emitting element or for irrigation via one or more exit ports in the housing.

The light emitting tip can include a hollow tube having a proximal end joined to the light transmitting optical fiber, a closed distal end, and an inner space defining a chamber therebetween. The light scattering medium disposed within the chamber can be a polymeric or liquid material having light scattering particles, such as alumina, silica, or titania compounds or mixtures thereof, incorporated therein. The distal end of the tube can include a reflective end and, optionally, the scattering medium and the reflective end can interact to provide a substantially uniform axial distribution of radiation over the length of the housing.

Alternatively, the light emitting tip can include at least one reflector for directing the radiation through the transmissive region of the housing toward a target site and, optionally can further include a plurality of reflectors and/or at least one defocusing lens for distributing the radiation in an elongated pattern.

The light emitting tip can further include at least one longitudinal reflector or similar optical element such that the radiation distributed by the tip is confined to a desired angular distribution.

The hand held instruments can include a handle incorporated into the housing. An inner lumen can extend through the handle to received the light delivering element. The distal end of the instrument can be resiliently deformable or malleable to allow the shape of the ablation element to be adjusted based on the intended use.

In one embodiment, a hand held cardiac ablation instrument is provided having a housing with a curved shape and at least one lumen therein. A light delivering element is disposable within the lumen of the housing for delivering ablative radiation to form a curved lesion at a target tissue site adjacent to the housing.

In another aspect of the invention, the light delivering element can be slidably disposed within the inner lumen of the housing, and can include a light transmitting optical fiber adapted to receive ablative radiation from a radiation source and a light diffusing tip at a distal end of the fiber for emitting radiation. The instrument can optionally include a handle joined to the housing and having an inner lumen though which the light delivering element can pass from the radiation source to the housing.

In another aspect of the present invention, the light diffusing tip can include a tube having a proximal end mated to the light transmitting optical fiber, a closed distal end, and an inner chamber defined therebetween. A light scattering medium is disposed within the inner chamber of the tube. The distal end of the tube can include a reflective end surface, such as a mirror or gold coated surface. The tube can also include a curved, longitudinally-extending, reflector that directs the radiant energy towards the target ablation site. The reflective surfaces and the light scattering medium interact to provide a substantially uniform axial distribution of radiation of the length of the housing.

In other aspects of the present invention, a hand held cardiac ablation instrument is provided having a slidably disposed light transmitting optical fiber, a housing in the shape of an open loop and having a first end adapted to receive the slidably disposed light transmitting optical fiber, and at least one diffuser chamber coupled to the fiber and disposed within the housing. The diffuser chamber can include a light scattering medium disposed within the housing and coupled to the slidably disposed light transmitting optical fiber.

In yet another aspect, a percutaneous cardiac ablation instrument in the form of a balloon catheter with an ablative light projecting assembly is provided. The balloon catheter instrument can include at least one expandable membrane disposed about a housing. This membrane is generally or substantially sealed and serves as a balloon to position the device within a lumen. The balloon structure, when filled with fluid, expands and is engaged in contact with the tissue. The expanded balloon thus defines a staging from which to project ablative radiation in accordance with the invention. The instrument can also include an irrigation mechanism for delivery of fluid at the treatment site. In one embodiment, irrigation is provided by a sheath, partially disposed about the occluding inner balloon, and provides irrigation at a treatment site (e.g. so that blood can be cleared from an ablation site). The entire structure can be deflated by applying a vacuum which removes the fluid from the inner balloon. Once fully deflated, the housing can be easily removed from the body lumen.

The present invention also provides methods for ablating tissue. One method of ablating tissue comprises positioning a distal end of a penetrating energy instrument in proximity to a target region of tissue, the instrument including a source of penetrating energy disposed within the distal end. The distal end of the instrument can be curved to permit the distribution of penetrating energy in elongated and/or arcuate patterns. The method further including activating the energy element to transmit penetrating energy to expose the target region and induce a lesion; and, optionally, repeating the steps of positioning and exposing until a composite lesion of a desired shape is formed.

In another method, a device is provided having a light delivering element coupled to a source of photoablative radiation and configured in a curved shape to emit an arcuate pattern of radiation. The device is positioned in proximity to a target region of cardiac tissue, and applied to induce a curvilinear lesion. The device is then moved to the second position and reapplied to induce a second curvilinear lesion. The steps of positioning and reapplying can be repeated until the lesions are joined together to create a composite lesion (e.g., a closed loop encircling one or more cardiac structures).

In another embodiment, methods of ablating cardiac tissue are provided. A device is provided having a housing in the shape of a hollow ring or partial ring having at least one lumen therein and at least one open end, and a light delivering element slidably disposed within the lumen of the housing for delivering ablative radiation to form a circular lesion at a target region adjacent the housing. The methods includes the steps of positioning the device in proximity to the target region of cardiac tissue, applying the device to the target region to induce a curvilinear lesion, advancing the light delivering element to a second position, reapplying the device to the target region to induce a second curvilinear lesion, and repeating the steps of advancing and applying until the lesions are joined together to create a composite circumferential lesion.

BRIEF DESCRIPTION OF THE DRAWINGS

The invention will be more fully understood from the following detailed description taken in conjunction with the accompanying drawings, in which like reference numerals designate like parts throughout the figures, and wherein.

DETAILED DESCRIPTION

Figure 1:
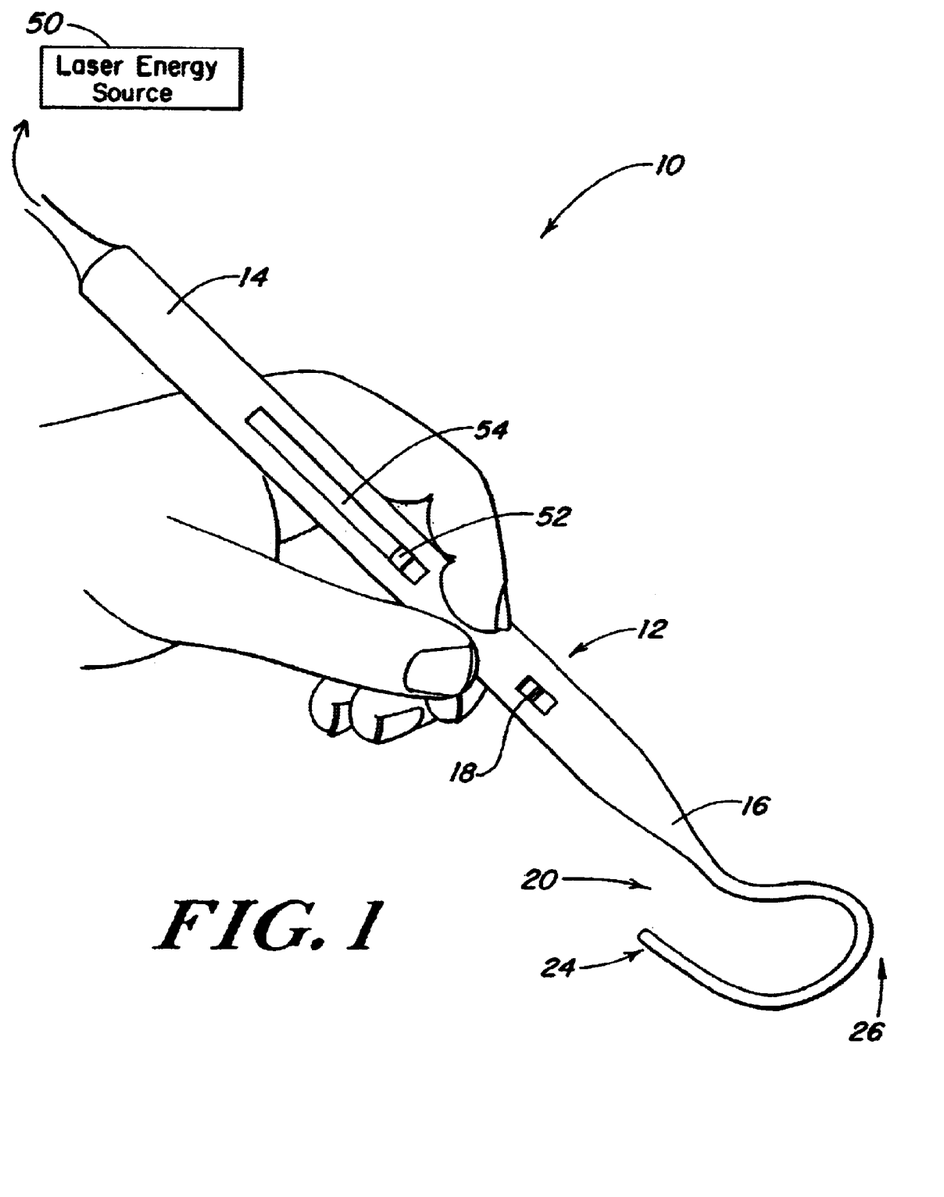
FIG. 1 is a schematic, perspective view of a hand held surgical ablation instrument in accordance with this invention.

The present invention provides a hand held surgical ablation instrument that is useful, for example, for treating patients with atrial arrhythmia. As shown in FIG. 1, the hand held cardiac ablation instrument 10 generally includes a handle 12 having a proximal end 14 and a distal end 16, an ablation element 20 mated to or extending distally from the distal end 16 of the handle 12, and a penetrating energy source 50. The energy source 50 can be, for example, a laser source of radiation, e.g., coherent light, which can be efficiently and uniformly distributed to the target site while avoiding harm or damage to surrounding tissue. In use, the instrument can be applied either endocardially or epicardially, and is effective to uniformly irradiate a target ablation site.

The handle 12 of the ablation instrument 10 is effective for manually placing the ablation element 20 proximate to a target tissue site. While the handle 12 can have a variety of shapes and sizes, preferably the handle is generally elongate with at least one inner lumen extending therethrough. The proximal end 14 of the handle 12 can be adapted for coupling with a source of radiant energy 50, and the distal end of the handle 16 is mated to or formed integrally with the ablation element 20. In a preferred embodiment, the handle 12 is positioned substantially coaxial with the center of the ablation element 20. The handle 14 can optionally include an on-off switch 18 for activating the laser energy source 50.

Figure 1A:
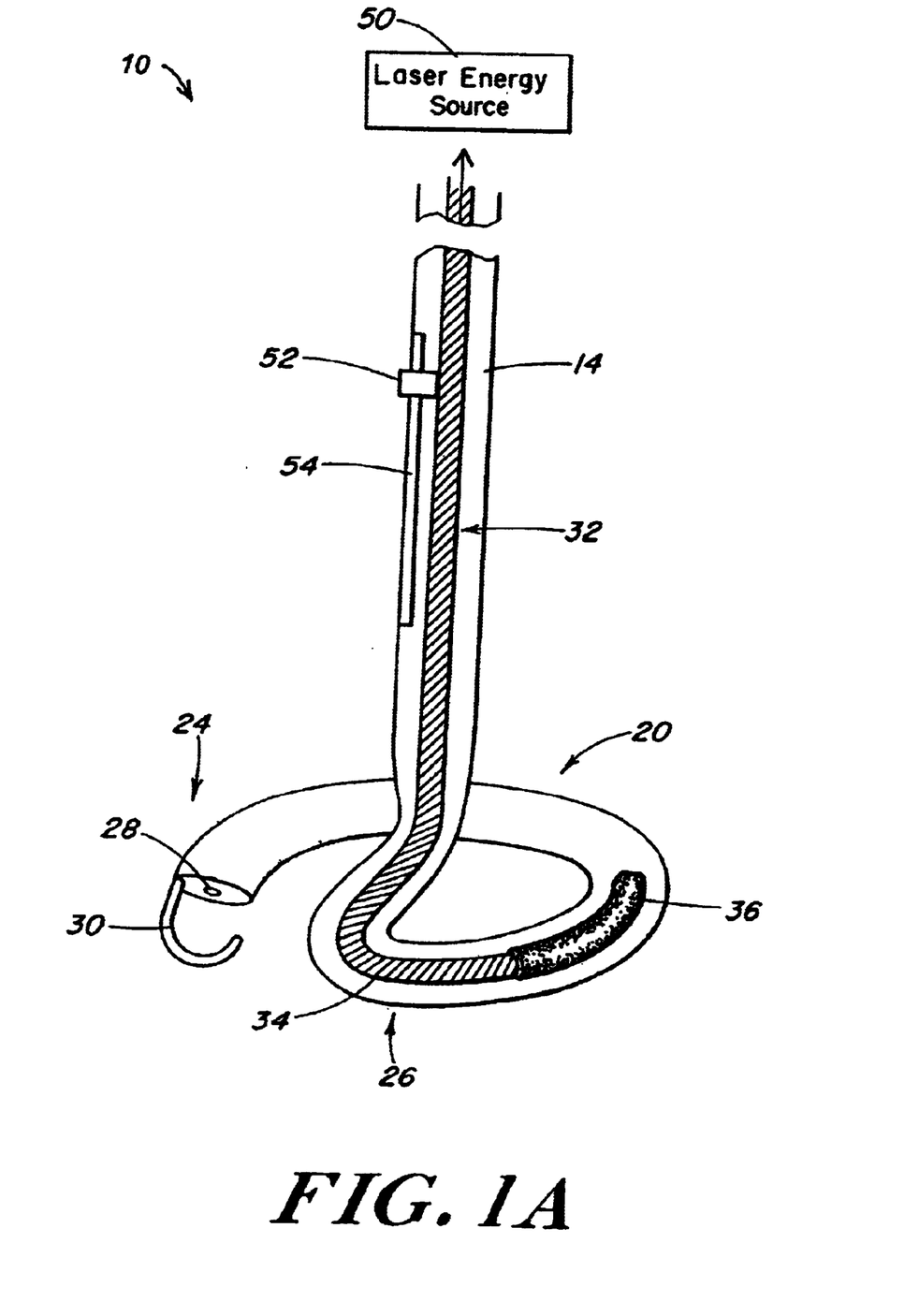
FIG. 1A is a partially cross-sectional view of the hand held surgical ablation instrument of FIG. 1.
Figure 2:
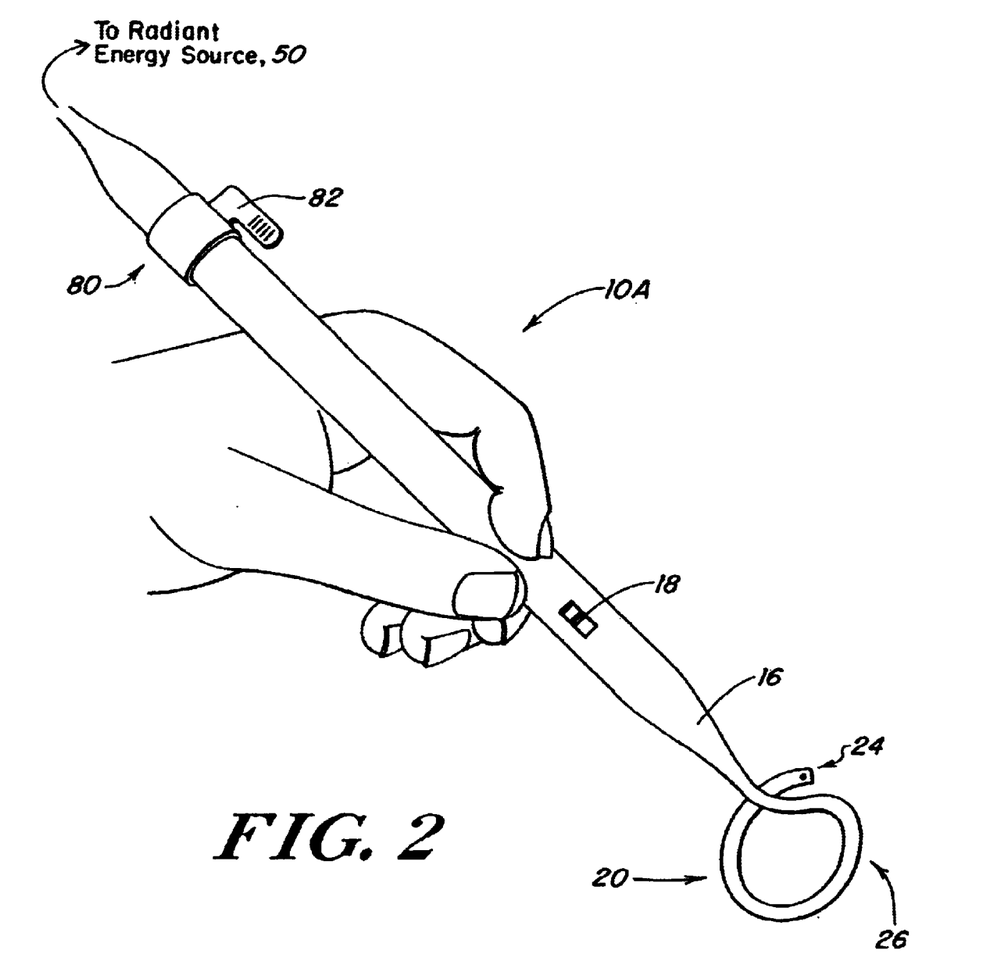
FIG. 2 is a schematic, perspective view of another embodiment of a hand held surgical ablation instrument in accordance with this invention.

One circumferential ablation element 20 is shown in more detail in FIG. 1A, and includes an outer housing 22 having an inner lumen extending therethrough, and a light delivering element 32 disposed within the inner lumen of the outer housing 22. The outer housing 22 can be flexible, and is preferably malleable to allow the shape of the outer housing 22 to be adapted based on the intended use. As shown in FIG. 2, the outer housing 22 can be in the shape of a hollow ring (or partial ring) forming an opening loop having leading and trailing ends 24, 26. The open loop-shape allows the circumferential ablation element 20 to be positioned around one or more pulmonary veins. While an open loop shape is illustrated, the outer housing 22 can also be formed or positioned to create linear or other shaped lesions.

The housing can be made from a variety of materials including polymeric, electrically nonconductive material, like polyethylene or polyurethane, which can withstand tissue coagulation temperatures without melting. Preferably, the housing is made of Teflon® tubes and/or coatings. The use of Teflon® improves the procedures by avoiding the problem of fusion or contact-adhesion between the ablation element 12 and the cardiac tissue during usage. While the use of Teflon® avoids the problem of fusion or contact-adhesion, the hand held cardiac ablation instrument 10 does not require direct contact with the tissue to effect a therapeutic or prophylactic treatment.

The outer housing 22 can optionally include a connecting element for forming a closed-loop circumferential ablation element 20. By non-limiting example, FIG. 1A illustrates a connecting element 30 extending from the leading, distal end 24 of the outer housing 22. The connecting element 30 has a substantially u-shape and is adapted for mating with the trailing end 26 of the outer housing 22 or the distal end 16 of the handle 12. The connecting element 30 can optionally be adapted to allow the size of the circumferential ablation element is 20 to be adjusted once positioned around the pulmonary veins. For example, the connecting element 30 can be positioned around the trailing end 26 of the outer housing 22 after the circumferential ablation element 20 is looped around the pulmonary veins, and the handle 12 can then be pulled to cause the ablation element 20 to tighten around the pulmonary veins. While FIG. 1A illustrates a U-shaped connecting element, a person having ordinary skill in the art will appreciate that a variety of different connecting elements or clasps 30 can be used such as, for example, a hook, a cord, a snap, or other similar connecting device.

The light delivering element 32 which is disposed within the outer housing 22 includes a light transmitting optical fiber 34 and a light diffusing tip 36. The light transmitting optical fiber 34 is effective for delivering radiant energy from the laser energy source 50 to the light diffusing tip 36, wherein the laser energy is diffused throughout the tip 36 and delivered to the target ablation site. The light delivering element 32 can be slidably disposed within the outer housing to allow the light diffusing tip 36 to be positioned with respect to the target ablation site. A lever 52 or similar mechanism can be provided for slidably moving the light delivering element 32 with respect to the handle 12. As shown in FIG. 1A, the lever 52 can be mated to the light delivering element 32 and can protrude from a distally extending slot 54 formed in the handle 12. Markings can also be provided on the handle for determining the distance moved and the length of the lesion formed. A person having ordinary skill in the art will readily appreciate that a variety of different mechanisms can be employed to slidably move the light delivering element 32 with respect to the handle 12.

Figure 2A:
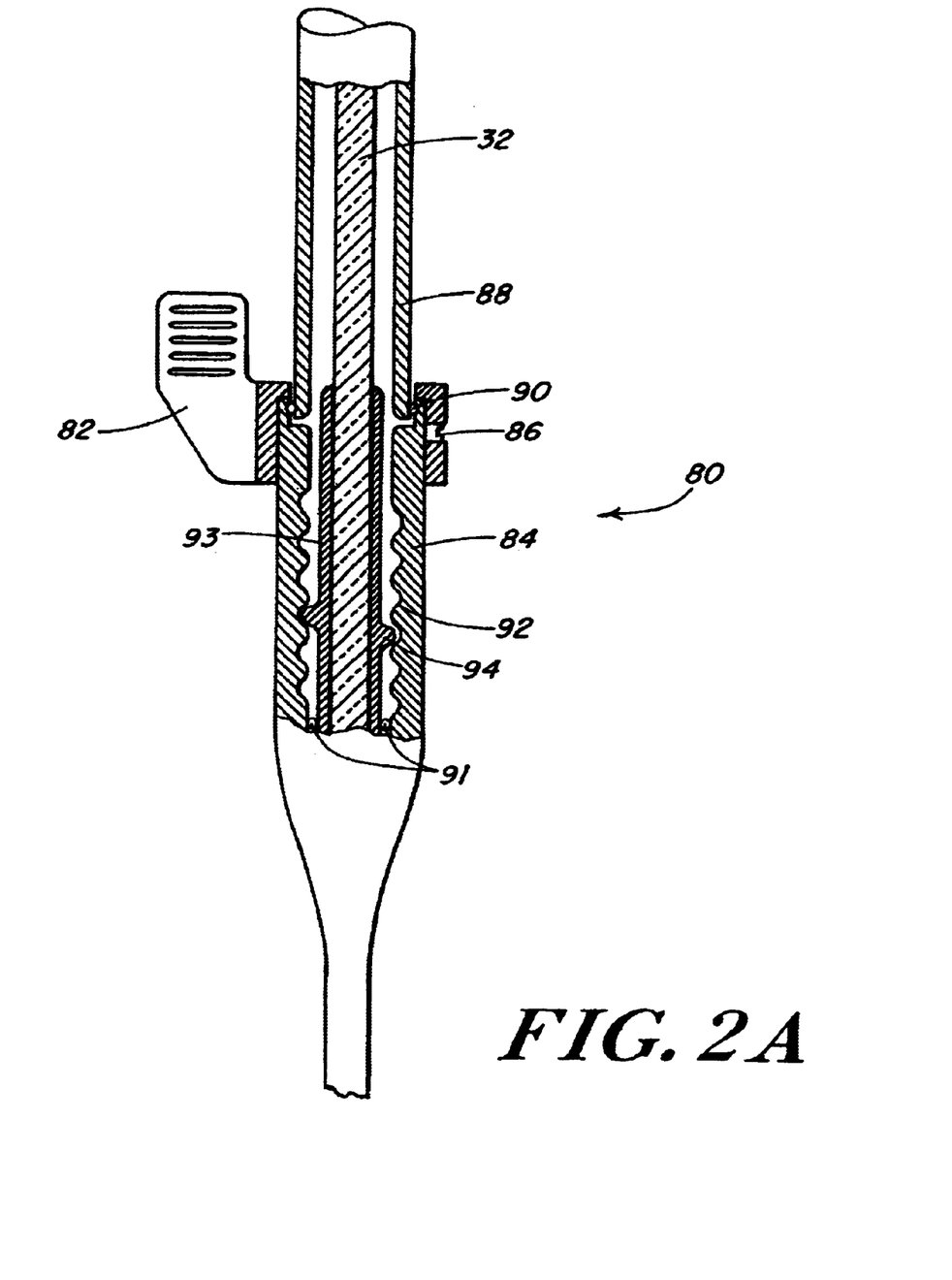
FIG. 2A is a partially cross-sectional view of the hand held surgical ablation instrument of FIG. 2.

Another embodiment of the surgical ablation instrument 10A is shown in FIG. 2, where a rotatable lever 82 can be used to control the positioning of a light delivery element in the distal tip of the instrument. The lever 82 turns a translatory mechanism 80, as shown in more detail in FIG. 2A. In this embodiment, a portion 84 of the handle is separated from the rest of the housing 88 such that it can rotate, and preferably sealed by O-rings 90 and 91, or the like. The rotatable segment 84 has internal screw threads 92. Within this segment of the handle, the light delivering fiber 32 is joined to a jacket 93 that has an external screw thread 94. The threads 94 of jacket 93 mate with the threads 92 of rotatable segment 84. The lever 82 is affixed to rotatable segment 84 (e.g., by set screw 86) such that rotation of knob 82 causes longitudinal movement of the fiber 32 relative to the housing 88.

The inner lumen of the outer housing 22 in FIGS. 1 and 2 can optionally contain a irrigating fluid to assist the light delivering element 32 as it is slidably movable within the outer housing 22. The fluid can also cool the light delivering element 32 during delivery of ablative energy. Fluid can be introduced using techniques known in the art, but is preferably introduced through a port and lumen formed in the handle. The distal end 24 of the outer housing 22 can include a fluid outflow port 28 for allowing fluid to flow therethrough.

Figure 3:
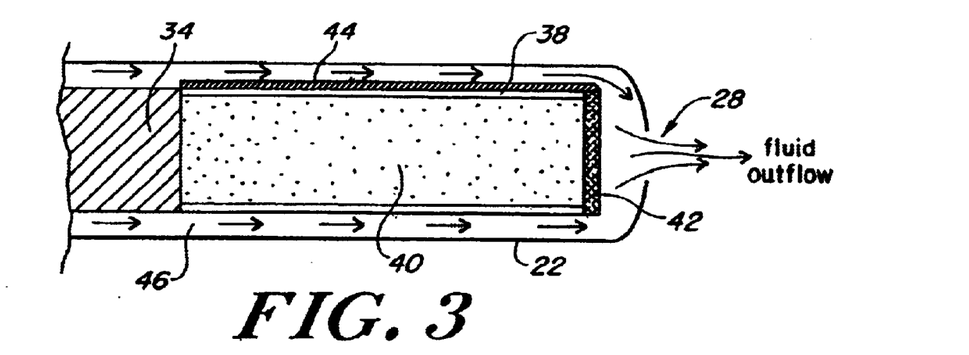
FIG. 3 is a schematic, side perspective view of a tip portion of an ablation instrument in accordance with this invention illustrating a light delivery element.

As shown in FIG. 3, the fluid travels between the light delivering element 32 toward the leading, distal end 26 of the outer housing 22 and exits the fluid outflow port 28. Since the port 28 is positioned on the distal end 26 of the outer housing 22, the fluid does not interfere with the ablation procedure. While FIG. 3 illustrates the fluid outflow port 28 disposed on the distal end 24 of the outer housing 22, a person having ordinary skill in the art will readily appreciate that the fluid outflow port 28 can be disposed anywhere along the length of the outer housing 22.

Figure 3A:
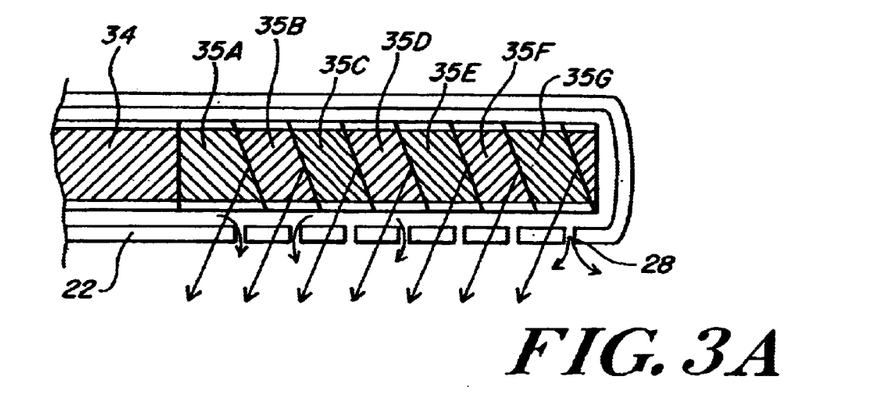
FIG. 3A is a schematic, side perspective view of a tip portion of another ablation instrument in accordance with this invention.

In FIG. 3A another embodiment of a light delivery element according to the invention is shown in fiber 34 terminates in a series of partially reflective elements 35A–35G. (It should be appreciated that the number of reflective elements can vary depending on the application and the choice of six is merely for illustration.) The transmissivity of the various segments can controlled such that, for example, segment 35A is less reflective than segment 35B, which in turn is less reflective than 35C, etc., in order to achieve uniform diffusion of the light. The reflective elements of FIG. 3A can also be replaced, or augmented, by a series of light scattering elements having similar progressive properties. FIG. 3A also illustrates another arrangement of exit ports 28 in housing 22 for fluid, whereby the fluid can be used to irrigate the target site.

With reference again to FIG. 3, the light transmitting optical fiber 34 generally includes an optically transmissive core surrounded by a cladding and a buffer coating (not shown). The optical fiber 34 should be flexible to allow the fiber 34 to be slidably moved with respect to the handle 12. In use, the light transmitting optical fiber 34 conducts light energy in the form of ultraviolet light, infrared radiation, or coherent light, e.g., laser light. The fiber 34 can be formed from glass, quartz, polymeric materials, or other similar materials which conduct light energy.

The light diffusing tip 36 extends distally from the optical fiber 34 and is formed from a transmissive tube 38 having a light scattering medium 40 disposed therein. For additional details on construction of light diffusing elements, see, for example, U.S. Pat. No. 5,908,415 issued Jun. 1, 1999.

The scattering medium 40 disposed within the light diffusing tip 36 can be formed from a variety of materials, and preferably includes light scattering particles. The refractive index of the scattering medium 40 is preferably greater than the refractive index of the housing 22. In use, light propagating through the optical fiber 34 is transmitted through the light diffusing tip 36 into the scattering medium 40. The light is scattered in a cylindrical pattern along the length of the light diffusing tip 36 and, each time the light encounters a scattering particle, it is deflected. At some point, the net deflection exceeds the critical angle for internal reflection at the interface between the housing 22 and the scattering medium 40, and the light exits the housing 22 to ablate the tissue.

Preferred scattering medium 40 includes polymeric material, such as silicone, epoxy, or other suitable liquids. The light scattering particles can be formed from, for example, alumina, silica, or titania compounds, or mixtures thereof. Preferably, the light diffusing tip 36 is completely filled with the scattering medium 40 to avoid entrapment of air bubbles.

As shown in more detail in FIG. 3, the light diffusing tip 36 can optionally include a reflective end 42 and/or a reflective coating 44 extending along a length of one side of the light diffusing tip 36 such that the coating is substantially diametrically opposed to the target ablation site. The reflective end 42 and the reflective coating 44 interact to provide a substantially uniform distribution of light throughout the light diffusing tip 36. The reflective end 42 and the reflective coating 44 can be formed from, for example, a mirror or gold coated surface. While FIG. 3 illustrates the coating extending along one side of the length of the diffusing tip 36, a person having ordinary skill in the art will appreciate that the light diffusing tip 36 can be coated at different locations relative to the target ablation site. For example, the reflective coating 44 can be applied over 50% of the entire diameter of the light diffusing tip 36 to concentrate the reflected light toward a particular target tissue site, thereby forming a lesion having a relatively narrow width.

In one use, the hand held ablation instrument 10 is coupled to a source of penetrating energy 50 and can be positioned within a patient's body either endocardially or epicardially to ablate cardiac tissue. When the penetrating energy is light, the source is activated to transmit light through the optical fiber 34 to the light diffusing tip 36, wherein the light is scattered in a circular pattern along the length of the tip 36. The tube 38 and the reflective end 42 interact to provide a substantially uniform distribution of light throughout the tip 36. When a mirrored end cap 42 is employed, light propagating through the light diffusing tip 36 will be at least partially scattered before it reaches the mirror 42. When the light reaches the mirror 42, it is then reflected by the mirror 42 and returned through the tip 36. During the second pass, the remaining radiation encounters the scattering medium 40 which provides further diffusion of the light.

Figure 4:
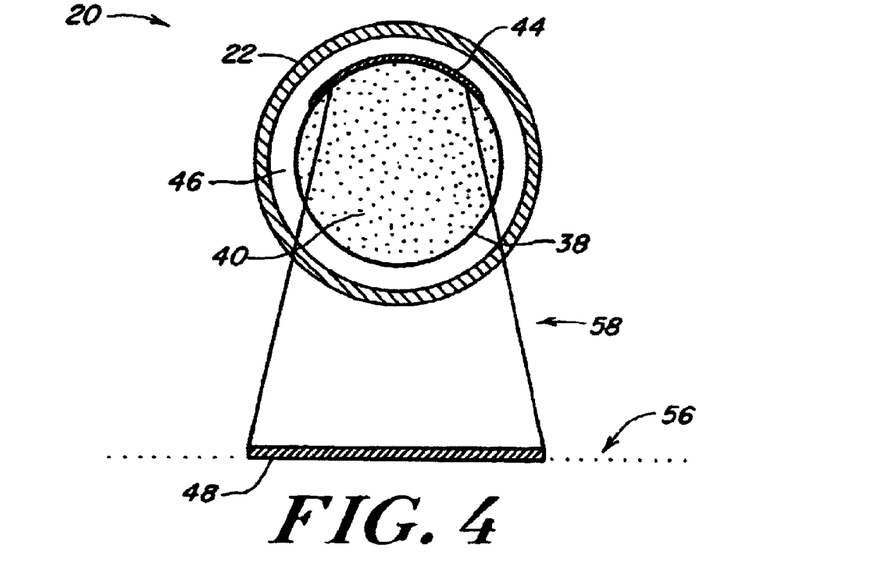
FIG. 4 is a schematic, cross sectional view of the light delivery element of FIG. 3.

When a reflective coating or longitudinally disposed reflector 44 is used, as illustrated in FIG. 4, the light 58 emitted by the diffusing tip 36 will reflected toward the target ablation site 56 to ensure that a uniform lesion 48 is created. The reflective coating or element 44 is particularly effective to focus or direct the light 58 toward the target ablation site 56, thereby preventing the light 58 from passing through the housing 22 around the entire circumference of the housing 22.

Figure 4A:
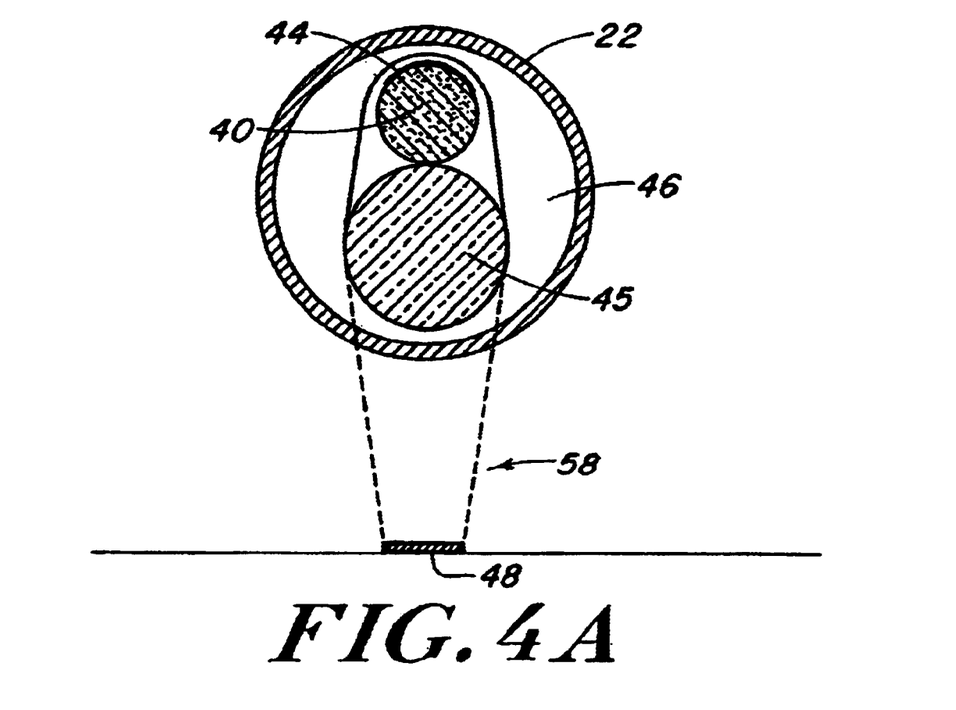
FIG. 4A is a schematic, cross sectional view of another embodiment of a light delivery element.

In another embodiment as illustrated in FIG. 4A, the light emitting element can further include a longitudinally extended lens element 45, such that light scattered by the scattering medium 40 is not only reflected by reflector 44 but also confined to a narrow angle.

Figure 4B:
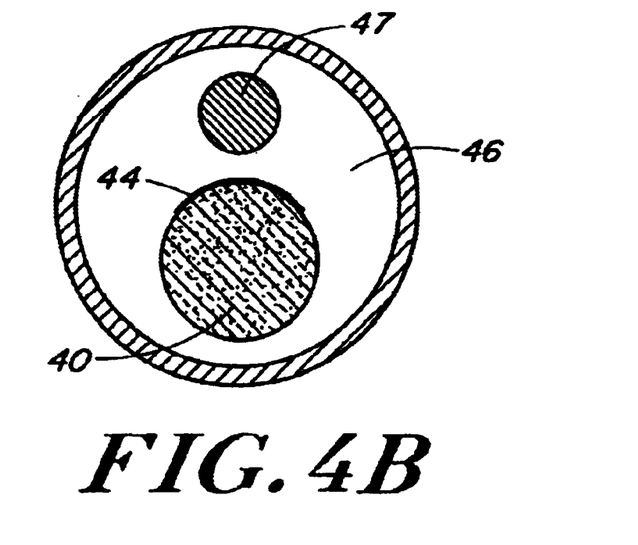
FIG. 4B is a schematic, cross sectional view of another embodiment of a light delivery element surrounded by a malleable housing.

In yet another embodiment of the invention, illustrated in FIG. 4B, the housing 22 that surrounds the light delivery element that include or surround a malleable element 47, e.g., a soft metal bar or strip such that the clinician can form the distal end of the instrument into a desired shape prior to use. Although the malleable element 47 is shown embedded in the housing 22, it should be clear that it can also be incorporated into the light delivery element (e.g., as part of the longitudinally extended reflector) or be distinct from both the housing and the light emitter.

Figure 5:
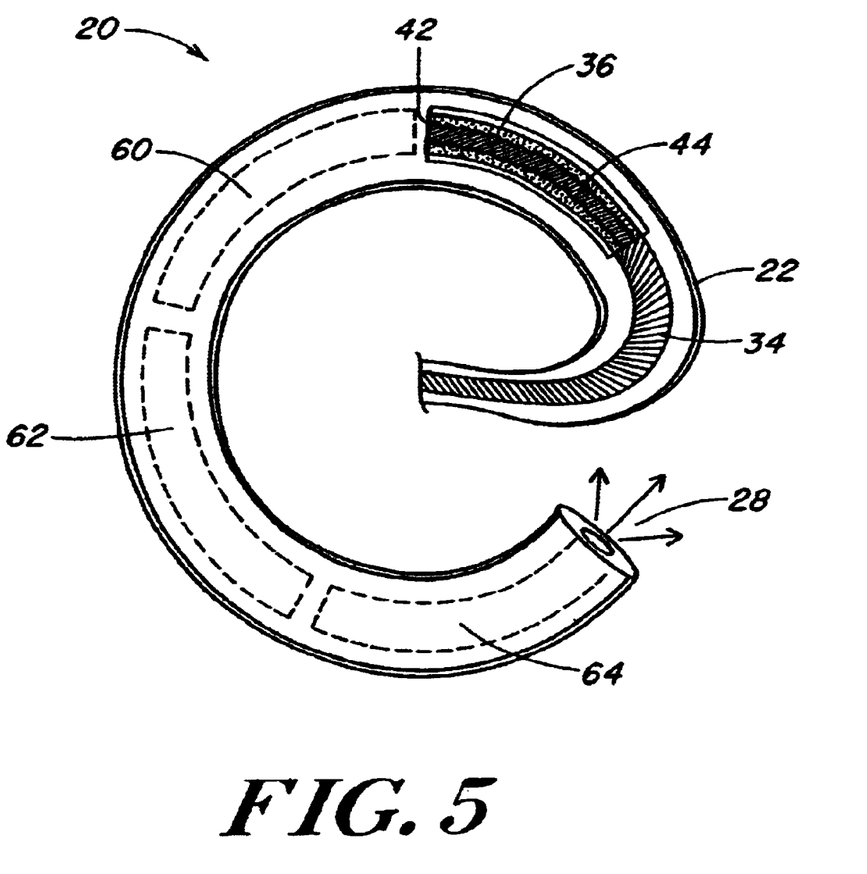
FIG. 5 is a schematic, cross sectional top view of a surgical ablation element of according to the invention, illustrating the different ablating positions of the light delivering element.

Epicardial ablation is typically performed during a by-pass procedure, which involves opening the patient's chest cavity to access the heart. The heart can be arrested and placed on a by-pass machine, or the procedure can be performed on a beating heart. The hand held ablation instrument 10 is placed around one or more pulmonary veins, and is preferably placed around all four pulmonary veins. The connecting element 30 can then be attached to the distal end 16 of the handle 12 or the proximal, trailing end 24 of the outer housing 22 to close the open loop. The handle 12 can optionally be pulled to tighten the ablation element 20 around the pulmonary veins. The energy delivering element 32 is then moved to a first position, as shown in FIG. 5, and the energy source 50 is activated ht. The first lesion is preferably about 4 cm in length, as determined by the length of the tip 36. Since the distance around the pulmonary veins is about 10 cm, the energy delivering element 32 is moved forward about 4 cm to a second position 60, shown in phantom in FIG. 5, and the tissue is ablated to create a second lesion. The procedure is repeated two more times, positioning the energy delivering element 32 in a third position 62 and a fourth position 64. The four lesions together can form a lesion 48 around the pulmonary veins, for example.

Figure 6:
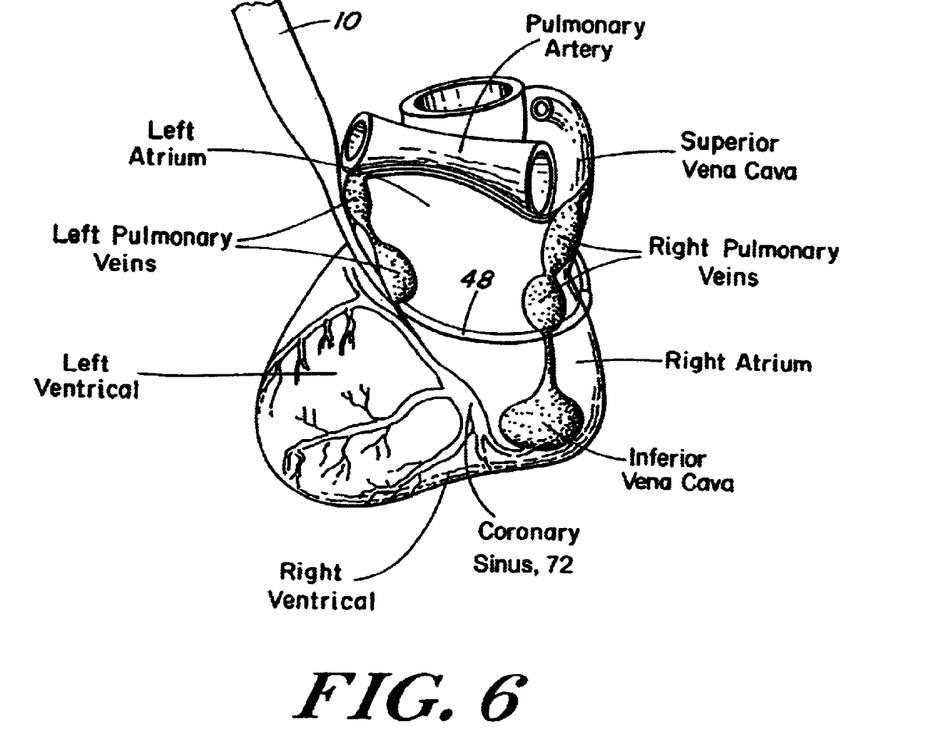
FIG. 6 is a schematic, perspective view of a human heart and an instrument according to the invention, showing one technique for creating epicardial lesions.

In another aspect of the invention, the instruments of the present invention are particularly useful in forming lesions around the pulmonary veins by directing radiant energy towards the epicardial surface of the heart and the loop configuration of distal end portion of the instruments facilitates such use. It has been known for some time that pulmonary veins can be the source of errant electrical signals and various clinicians have proposed forming conduction blocks by encircling one or more of the pulmonary veins with lesions. As shown in FIG. 6, the instrument 10 of the present invention is well suited for such ablation procedures. Because the pulmonary veins are located at the anterior of the heart muscle, they are difficult to access, even during open chest surgery. An open loop distal end is thus provided to encircle the pulmonary veins. The open loop can then be closed (or cinched tight) by a clasp, as shown. (The clasp can also take the form of suture and the distal end of the instrument can include one or more holes to receive such sutures as shown in FIG. 2.) The longitudinal reflector structures described above also facilitate such epicardial procedures by ensuring that the light from the light emitting element is directed towards the heart and not towards the lungs or other adjacent structures.

Figure 7:
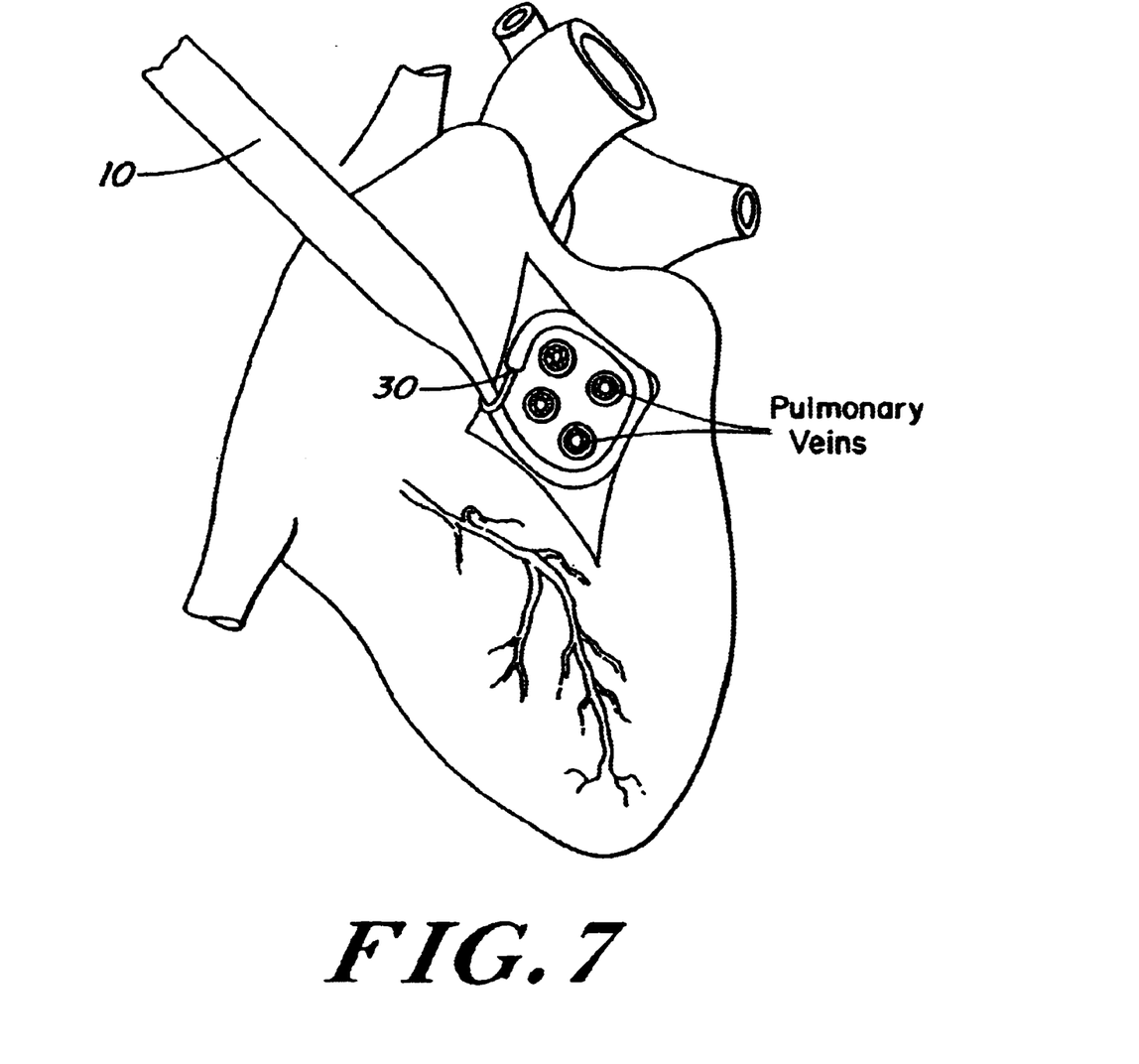
FIG. 7 is a schematic, perspective view of a human heart and an instrument according to the invention, showing one technique for creating endocardial lesions.
Figure 8:
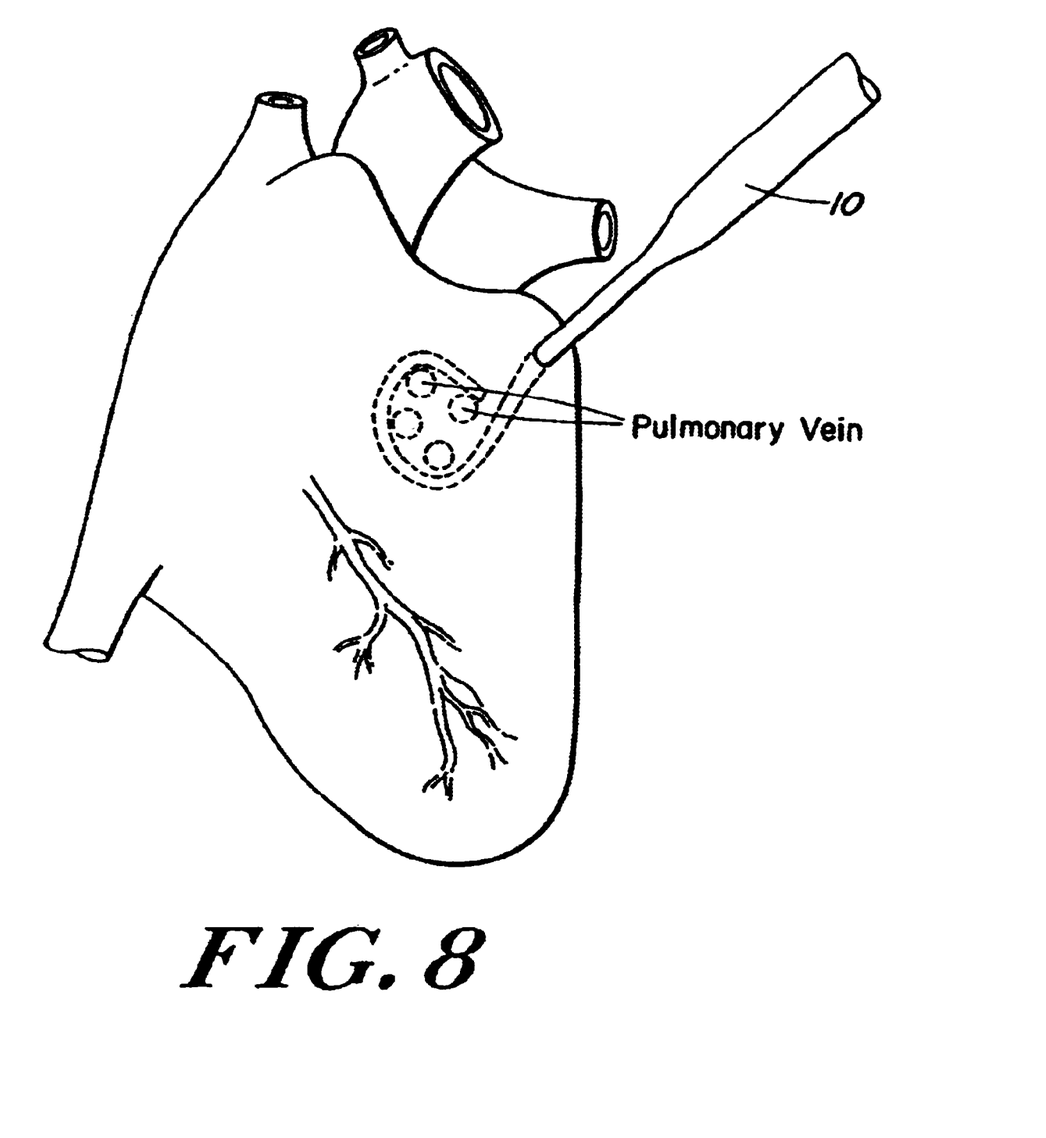
FIG. 8 is a schematic, perspective view of a human heart and an instrument according to the invention, showing another technique for creating endocardial lesions.

Endocardial applications, on the other hand, are typically performed during a valve replacement procedure which involves opening the chest to expose the heart muscle. The valve is first removed, and then the hand held cardiac ablation instrument 10 according to the present invention is positioned inside the heart as shown in FIG. 7. In another approach the instrument 10 can be inserted through an access port as shown in FIG. 8. The ablation element 20 can be shaped to form the desired lesion, and then positioned at the atrial wall around the ostia of one or more of the pulmonary veins. Once shaped and positioned, the laser energy source 50 is activated to ablate a first portion of tissue. The light delivering element 32 can then be slidably moved, as described above with respect to the epicardial application, or alternatively, the entire device can be rotated to a second position to form a second lesion.

Preferred energy sources for use with the hand held cardiac ablation instrument 10 and the balloon catheter 150 of the present invention include laser light in the range between about 200 nanometers and 2.5 micrometers. In particular, wavelengths that correspond to, or are near, water absorption peaks are often preferred. Such wavelengths include those between about 805 nm and about 1060 nm, preferably between about 900 nm and 1000 nm, most preferably, between about 915 nm and 980 nm. In a preferred embodiment, wavelengths around 915 nm are used during epicardial procedures, and wavelengths around 980 nm are used during endocardial procedures. Suitable lasers include excimer lasers, gas lasers, solid state lasers and laser diodes. One preferred AlGaAs diode array, manufactured by Optopower, Tucson, Ariz., produces a wavelength of 980 nm. Typically the light diffusing element emits between about 2 to about 10 watts/cm of length, preferably between about 3 to about 6 watts/cm, most preferably about 4 watts/cm.

The term "penetrating energy" as used herein is intended to encompass energy sources that do not rely primarily on conductive or convective heat transfer. Such sources include, but are not limited to, acoustic and electromagnetic radiation sources and, more specifically, include microwave, x-ray, gamma-ray, and radiant light sources.

The term "curvilinear," including derivatives thereof, is herein intended to mean a path or line which forms an outer border or perimeter that either partially or completely surrounds a region of tissue, or separate one region of tissue from another. Further, a "circumferential" path or element may include one or more of several shapes, and may be for example, circular, annular, oblong, ovular, elliptical, or toroidal. The term "clasp" is intended to encompass various types of fastening mechanisms including sutures and magnetic connectors as well as mechanical devices. The term "light" is intended to encompass radiant energy, whether or not visible, including ultraviolet, visible and infrared radiation.

The term "lumen," including derivatives thereof, is herein intended to mean any elongate cavity or passageway.

The term "transparent" is well recognized in the art and is intended to include those materials which allow transmission of energy. Preferred transparent materials do not significantly impede (e.g., result in losses of over 20 percent of energy transmitted) the energy being transferred from an energy emitter to the tissue or cell site. Suitable transparent materials include fluoropolymers, for example, fluorinated ethylene propylene (FEP), perfluoroalkoxy resin (PFA), polytetrafluoroethylene (PTFE), and ethylenetetrafluoroethylene (ETFE).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of ablating cardiac tissue, comprising:
   positioning a distal portion of a photoablation instrument having an open loop shape around at least one pulmonary vein, the instrument having a housing with a lumen and a light delivering element coupled to a source of photoablative radiation and within the distal portion, the distal portion being transmissive to a selected wavelength of ablative radiation to permit the distribution of radiation by the light delivering element in a pattern;
   activating the light delivering element to transmit tissue penetrating radiant energy through the housing to deposit energy through the full thickness of the cardiac tissue and thereby form a transmural lesion.

2. The method of claim 1, wherein the method further comprises distributing photoablative radiation in an elongated pattern.

3. The method of claim 1, wherein the instrument is curved and the method further comprises distributing photoablative radiation in an elongated arcuate pattern.

4. The method of claim 1, wherein the distal end of the instrument is malleable and the method further comprises shaping the distal end into a loop having a radius between about 5 and 25 mm.

5. The method of claim 1, wherein the method further comprises:
   repeating the steps of positioning and exposing until a composite lesion of a desired shape is formed.

6. The method of claim 1, wherein the method further comprises generating phoroablative radiation at a desired wavelength ranging from about 800 nm to about 1000 nm.

7. The method of claim 1, wherein the method further comprises generating photoablative radiation at a desired wavelength ranging from about 915 nm to about 980 nm.

8. The method of claim 1, wherein the method further comprises generating photoablative radiation at a wavelength of about 915 nm.

9. The method of claim 1, wherein the method further comprises generating photoablative radiation at a wavelength of about 980 nm.

10. A method of treating cardiac arrhythmias, comprising:
    positioning an open loop of an ablation instrument around at least one pulmonary vein in proximity to a target cardiac treatment site, the instrument including a source of radiant energy; and
    activating the instrument to transmit tissue penetrating radiant energy into cardiac tissue at the target site to form a transmural lesion by uniform heating of the target tissue.

11. A method of treating cardiac arrhythmias, comprising:
    positioning an ablation instrument in proximity to a target cardiac treatment site, the instrument including a source of radiant energy; and
    activating the instrument to transmit tissue penetrating radiant energy into cardiac tissue at the target site to form a transmural lesion by uniform heating of the target tissue;
    wherein the distal end of the instrument is malleable and the method further comprises shaping the distal end into a loop having a radius between about 5 and 25 mm.

12. A method of ablating cardiac tissue, comprising:
    positioning a distal portion of a photoablation instrument in proximity to a target region of cardiac tissue, the instrument having a housing with a lumen and a light delivering element coupled to a source of photoablative radiation and within the distal portion, the distal portion being transmissive to a selected wavelength of ablative radiation to permit the distribution of radiation by the light delivering element in a pattern;

activating the light delivering element to transmit tissue penetrating radiant energy through the housing to deposit energy through the full thickness of the cardiac tissue and thereby form a transmural lesion;

wherein the distal end of the instrument is malleable and the method further comprises shaping the distal end into a loop having a radius between about 5 and 25 mm.

13. The method of claim 12, wherein the method further comprises distributing photoablative radiation in an elongated pattern.

14. The method of claim 12, wherein the instrument is curved and the method further comprises distributing photoablative radiation in an elongated arcuate pattern.

15. The method of claim 12, wherein the method further comprises:

repeating the steps of positioning and exposing until a composite lesion of a desired shape is formed.

16. The method of claim 12, wherein the method further comprises generating photoablative radiation at a desired wavelength ranging from about 800 nm to about 1000 nm.

17. The method of claim 12, wherein the method further comprises generating photoablative radiation at a desired wavelength ranging from about 915 nm to about 980 nm.

18. The method of claim 12, wherein the method further comprises generating photoablative radiation at a wavelength of about 915 nm.

19. The method of claim 12, wherein the method further comprises generating photoablative radiation at a wavelength of about 980 nm.

20. The method of claim 12, wherein the method further comprises generating photoablative radiation at a wavelength of about 980 nm.

* * * * *